United States Patent [19]

Harandi et al.

[11] Patent Number: 5,024,679
[45] Date of Patent: * Jun. 18, 1991

[54] OLEFINS ETHERIFICATION AND CONVERSION TO LIQUID FUELS WITH PARAFFINS DEHYDROGENATION

[75] Inventors: Mohsen N. Harandi, Lawrenceville; Hartley Owen, Belle Mead, both of N.J.

[73] Assignee: Mobil Oil Corporation, Fairfax, Va.

[*] Notice: The portion of the term of this patent subsequent to May 2, 2006 has been disclaimed.

[21] Appl. No.: 480,710

[22] Filed: Feb. 15, 1990

Related U.S. Application Data

[63] Continuation-in-part of Ser. No. 179,729, Apr. 11, 1988, abandoned, which is a continuation-in-part of Ser. No. 130,261, Dec. 8, 1987, Pat. No. 4,826,507, and a continuation-in-part of Ser. No. 130,259, Dec. 8, 1987, Pat. No. 4,830,635.

[51] Int. Cl.⁵ .................... C10L 1/18; C07C 41/06
[52] U.S. Cl. ........................ 44/449; 568/697; 568/699
[58] Field of Search ................ 44/77, 53, 449; 585/310

[56] References Cited

U.S. PATENT DOCUMENTS

| | | | |
|---|---|---|---|
| 4,191,846 | 3/1980 | Farah, Jr. et al. | 585/660 |
| 4,193,770 | 3/1980 | Chase et al. | 44/56 |
| 4,252,541 | 2/1981 | Herbstman | 568/697 |
| 4,329,516 | 5/1982 | Al-Muddarris | 568/697 |
| 4,377,393 | 3/1983 | Schleppinghoff | 44/53 |
| 4,413,150 | 11/1983 | Briggs | 568/697 |
| 4,826,507 | 5/1989 | Harandi et al. | 44/77 |
| 4,827,046 | 5/1989 | Harandi et al. | 585/310 |
| 4,830,635 | 5/1989 | Harandi et al. | 44/56 |

Primary Examiner—Prince E. Willis
Assistant Examiner—Ellen M. McAvoy
Attorney, Agent, or Firm—Alexander J. McKillop; Charles J. Speciale; L. G. Wise

[57] ABSTRACT

An integrated process for the production of ether-rich liquid fuels containing MTBE and TAME by etherifying a hydrocarbon feedstock containing $C_{4+}$ isoalkenes in the presence of a high stoichiometric excess of lower alkyl alcohol. Unreacted alcohol and olefins are passed to a zeolite catalyzed conversion reactor under olefinic and oxygenates conversion condition whereby gasoline and light hydrocarbons are produced. The light hydrocarbon fraction comprising $C_4$-$C_5$ paraffins is dehydrogenated and $C_4$-$C_5$ olefins are recycled to the etherification reactor.

20 Claims, 1 Drawing Sheet

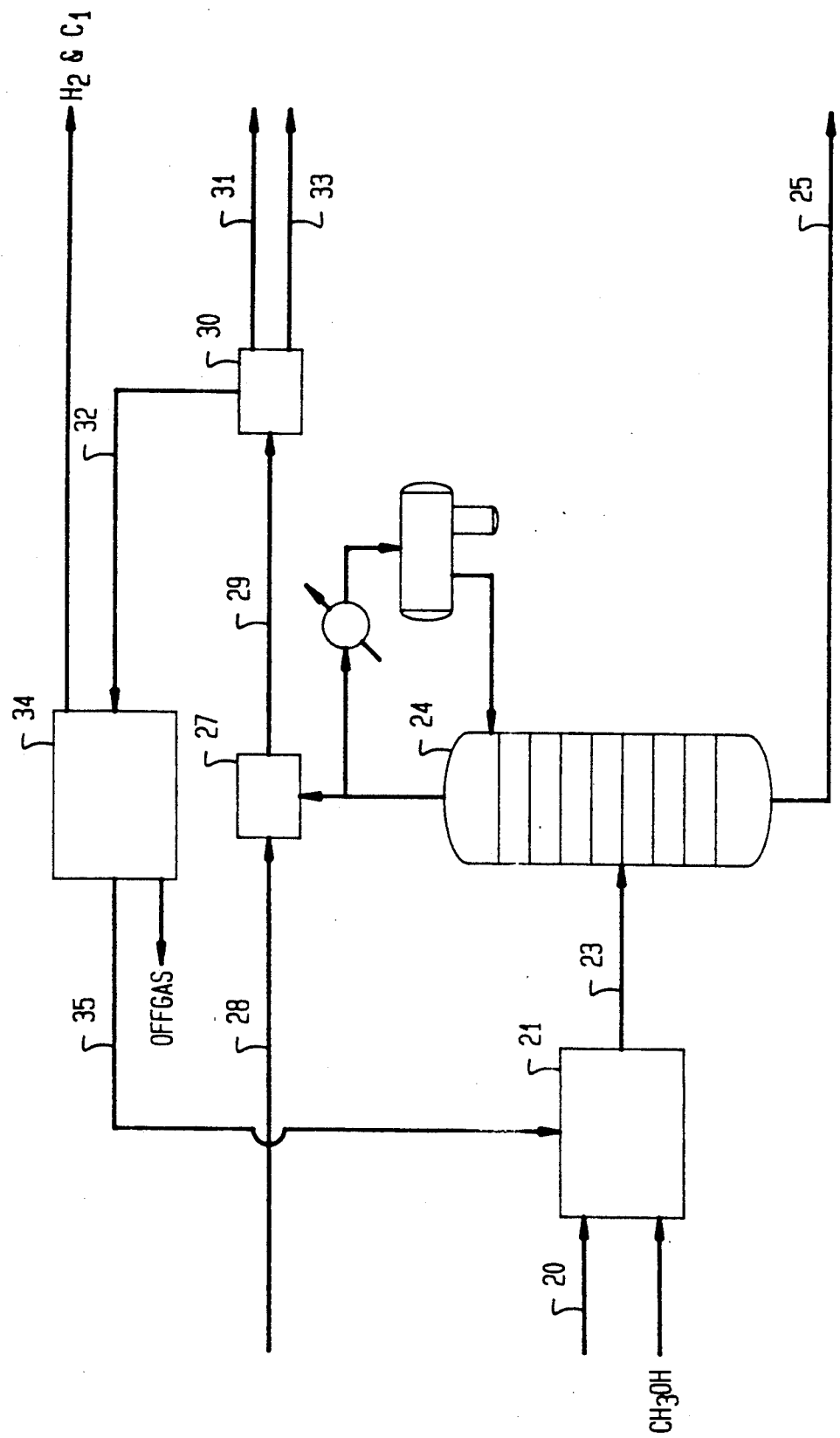

OLEFINS ETHERIFICATION AND CONVERSION TO LIQUID FUELS WITH PARAFFINS DEHYDROGENATION

REFERENCE TO COPENDING APPLICATION

This application is a continuation-in-part application of Ser. No. 179,729, filed Apr. 11, 1988 now abandoned, which is a continuation-in-part of U.S. patent application Ser. No. 07/130,261 filed Dec. 8, 1987, now U.S. Pat. No. 4,826,507, and a continuation-in-part of Ser. No. 07/130,259, filed Dec. 8, 1987, now U.S. Pat. No. 4,830,635, incorporated herein by reference.

BACKGROUND OF THE INVENTION

This invention relates to processes for converting methanol and olefinic hydrocarbons to high octane liquid fuel. In particular, this invention relates to a system for the production of methyl tertiary alkyl ethers in the presence of a high excess of methanol combined with the conversion of olefins to gasoline and dehydrogenation of paraffins to olefins.

In recent years, a major technical challenge presented to the petroleum refining industry has been the requirement to establish alternate processes for manufacturing high octane gasoline in view of the regulated requirement to eliminate lead additives as octane enhancers as well as the development of more efficient, higher compression ratio gasoline engines requiring higher octane fuel. To meet these requirements the industry has developed non-lead octane boosters and has reformulated high octane gasoline to incorporate an increased fraction of aromatics. While these and other approaches will fully meet the technical requirements of regulations requiring elimination of gasoline lead additives and allow the industry to meet the burgeoning market demand for high octane gasoline, the economic impact on the cost of gasoline is significant. Accordingly, workers in the field have intensified their effort to discover new processes to manufacture the gasoline products required by the market place. One important focus of that research is a new process to produce high octane gasolines blended with lower aliphatic alkyl ethers as octane boosters and supplementary fuels. $C_5$–$C_7$ methyl alkyl ethers, especially methyl tertiary butyl ether (MTBE) and tertiary amyl methyl ether (TAME) have been found particularly useful for enhancing gasoline octane. Therefore, improvements to the processes related to the production of these ethers are matters of high importance and substantial challenge to research workers in the petroleum refining arts.

It is known that isobutylene may be reacted with methanol over an acidic catalyst to provide methyl tertiary butyl ether (MTBE) and isoamylenes may be reacted with methanol over an acidic catalyst to produce tertiaryamyl methyl ether (TAME). In these etherification processes, a problem of major importance is that methanol is not totally converted and the separation of methanol from the etherification reaction product due to the proclivity of methanol to form a very dilute azeotropic mixture with hydrocarbons and the stron solubility of methanol in both water and hydrocarbons. While it would be beneficial from an equilibrium standpoint to use large excesses of methanol in etherification, subsequent separation problems have limited that process improvement. Due largely to these factors, the cost associated with conventional methanol separation and recycling in the etherification reaction represents approximately 30% of the cost of the total etherification process.

In U.S. Pat. No. 4,684,757 to Avidan et al., the well-known ability of zeolite type catalyst to convert methanol to olefins is utilized by directing unreacted methanol from an etherification reaction to a zeolite catalyzed conversion reaction for conversion to olefin, thereby obviating the need to separate and recycle methanol in the etherification reaction. However, the process of Avidan et al. converts oxygenate feedstock. The process incorporates an alkylation step in one embodiment to produce alkylate as well as $C_5+$ gasoline and $C_5+$ ethers.

The process for the conversion of methanol to olefins utilized in the Avidan et al. patent is but one in a series of analogous processes based upon the catalytic capabilities of zeolites. It is known that zeolites, such as ZSM-5, can convert methanol to hydrocarbons of higher average molecular weight. Depending on various conditions of space velocity, temperature and pressure methanol, and lower oxygenates in general, can be converted in the presence of zeolite type catalyst to olefins which may then oligomerize to provide gasoline or distillate or may be converted further to produce aromatics.

The feasibility and adaptability of the basic chemistry of zeolite oxygenates conversion to produce useful conversion processes has been the subject of much inventive research activity. Recent developments in zeolite catalyst and hydrocarbon conversion processes have created interest in using oxygenates and olefinic feedstocks for producing $C_5+$ gasoline, diesel fuel, etc. In addition to the basic work derived from ZSM-5 type zeolite catalyst, a number of discoveries have contributed to the development of a new industrial process. This process has significance as a safe, environmentally acceptable technique for utilizing feedstocks that contain lower olefins, especially $C_2$–$C_5$ alkenes. In U.S. Pat. Nos. 3,960,978 and 4,021,502, Plank, Rosinski and Givens disclose conversion of $C_2$–$C_5$ olefins, alone or in admixture with paraffinic components into higher hydrocarbons over crystalline zeolites having controlled acidity. Reaction conditions of moderate severity favor the conversion of olefins to predominantly gasoline boiling range products with little paraffins conversion. Milder reaction temperatures and high operating pressures can produce distillate range fuels as well from lower olefins. Garwood et al. have also contributed improved processing techniques in U.S. Pat. Nos. 4,150,062, 4,211,640 and 4,227,992. The above identified disclosures are incorporated herein by reference.

A well-known process for the conversion of oxygenates to gasoline is the methanol to gasoline process, known as MTG. The process is described in U.S. Pat. No. 3,931,349 to Kuo, U.S. Pat. No. 4,404,414 to Penick et al. and in the publication by C. D. Chang, Catal. Rev.-Sci. Eng., 25, 1 (1983). These references are incorporated herein in their entirety.

Recognizing the limiting problems of the etherification processes to produce MTBE and TAME and the potential that residues in the general area of the chemistry of oxygenate and olefin conversion with zeolites to resolve those problems, the following objectives of the instant invention have been established:

It is an object of the present invention to provide an improved process for the production of high octane gasoline incorporating methyl tertiaryalkyl ethers from isoalkene-rich hydrocarbons.

It is another object of the present invention to provide an integrated process for the production of liquid fuels from isoalkene-rich hydrocarbons incorporating etherification with methanol and olefins conversion and dehydrogenation of unreacted paraffins.

SUMMARY OF THE INVENTION

It has been discovered that high octane gasoline can be produced employing an improved etherification process that can utilize large stoichiometric excesses of lower alcohols such as methanol when the effluent from the etherification step containing unreacted methanol is separated and the excess methanol is passed to an oxygenates and olefins conversion step in contact with a metallosilicate catalyst, such as acid ZSM-5 medium pore aluminosilicate zeolite. In a particularly advantageous embodiment of the present invention, a portion of the etherification effluent containing unreacted paraffins as well as olefins is further separated after contact with the metallosilicate conversion catalyst and $C_4$–$C_5$ components are passed to a dehydrogenation zone in contact with a dehydrogenation catalyst to produce $C_4$–$C_5$ olefins which are recycled to the etherification zone. Optionally, $C_3$-hydrocarbons from the dehydrogenation step may be separated and passed to the olefins conversion zone containing metallosilicate catalyst such as zeolite ZSM-5.

More specifically, the invention comprises a process for the conversion of $C_2+$ hydrocarbons to ether-rich liquid fuels and high quality aliphatic/aromatic gasoline comprising;
(a) reacting a fresh hydrocarbon stream containing $C_4+$ isoalkenes with an excess of methanol in an etherification zone in contact with an acidic etherification catalyst under etherfication conditions whereby an effluent stream containing methyl tertiary alkyl ethers is produced;
(b) separating said etherification effluent stream to provide a first stream comprising ether-rich gasoline range hydrocarbons and a second stream comprising unreacted methanol and $C_4-$ or $C_5-$ hydrocarbons;
(c) contacting said second stream with an acidic metallosilicate catalyst in a conversion zone under olefins oligomerization conditions at elevated temperature;
(d) separating said conversion zone olefins oligomerization effluent stream into component streams comprising $C_4$–$C_5$ hydrocarbons, $C_3$ hydrocarbons and light gases, and $C_5+$ olefinic gasoline;
(e) contacting said $C_4$–$C_5$ hydrocarbon stream with a dehydrogenation catalyst under dehydrogenation conditions whereby $C_4$–$C_5$ paraffins are converted to olefins;
(f) separating the dehydrogenation effluent stream and passing the portion thereof comprising $C_4+$ olefins to said etherification zone in conjunction $C_4+$ olefins to said etherification zone in conjunction with said fresh hydrocarbon stream and methanol for conversion to methyl tertiaryalkyl ethers.

DESCRIPTION OF THE FIGURE

The single FIGURE is a schematic drawing of the process flow diagram of the instant invention.

DETAILED DESCRIPTION OF THE INVENTION

In the preferred embodiment of the instant invention the principal components of known processes are integrated in a manner providing a highly advantageous and surprising advancement in refinery technology leading to the production of high octane gasoline and distillate. Known processes are combined in a unique configuration that provides enhancement of the performance of component processes as well as achieving surprising advantages for the integrated process. The processes integrated include etherification to produce methyl tertiary butyl ether (MTBE) and methyl tertiary amyl ether (TAME), the conversion of methanol to gasoline, known as the MTG process, and the conversion of olefins to gasoline known as the MOG process. The MTO and MOG processes are closely related processes employing medium pore size shape selective zeolite type catalyst whose operating conditions are selected to shift the conversion reaction toward the production of olefins and the conversion of olefins to gasoline. The above processes are further integrated in a novel way through a dehydrogenation step to yield the fully integrated process of the instant invention. These known processes are discussed further herein. However, in FIG. 1, the fully integrated process of the present invention incorporating these individual processes is presented in a schematic drawing.

As known and employed in the present invention, the reaction of methanol with isobutylene and isoamylenes at moderate conditions with a resin catalyst is established technology, as provided by R. W. Reynolds, et al in *The Oil and Gas Journal*, June 16, 1975, and S. Pecci and T. Floris, *Hydrocarbon Processing*, December 1977. An article entitled "MTBE and TAME-a Good Octane Boosting Combo," by J. D. Chase, et al, *The Oil and Gas Journal*, Apr. 9, 1979, pages 149-152, discusses the technology. A preferred catalyst is a bifunctional ion exchange resin which etherifies and isomerizes the reactant streams. A typical acid catalyst is Amberlyst 15 sulfonic acid resin.

Processes for producing and recovering MTBE and other methyl tertiaryalkyl ethers from $C_4$–$C_7$ isolefins are known to those skilled in the art, such as disclosed in U.S. Pat. Nos. 4,544,776 (Osterburg, et al) and 4,603,225 (Colaianne, et al). Various suitable extraction and distillation techniques are known for recovering ether and hydrocarbon streams from etherification effluents.

In one segment of the present invention lower paraffins such as $C_4$–$C_5$ hyrocarbons from the olefins to gasoline conversion step are separated and passed to a dehydrogenation zone for dehydrogenation to olefins. It has been established that the conversion of paraffins, such as propane and butane, to mono-olefins, such as propylene and butylene, can be accomplished by thermal or catalytic dehydrogenation. A general discussion of thermal dehydrogenation (i.e., steam cracking) is presented in *Encyclopedia of Chemical Technology*, Ed. by Kirk and Othmer, Vol. 19, 1982, Third Ed., pp. 232-235. Various processes for catalytic dehydrogenation are available in the prior art. These processes include the Houdry Catofin process of Air Products and Chemical, Inc., Allentown, Pa., the Oleflex process of UOP, Inc., Des Moines, ILL. and a process disclosed by U.S. Pat. No. 4,191,846 to Farha, Jr. et al. The Houdry Catofin process, described in a magazine article, "Dehydrogenation Links LPG to More Octanes", Gussow et al, *Oil and Gas Journal*, Dec. 8, 1980, involves a fixed bed, multi-reactor catalytic process for conversion of paraffins to olefins. Typically, the process runs at low pressures of 5–30 inches of mercury absolute, and high temperatures with hot reactor effluent at 550°–650° C. Dehydrogenation is an endothermic reaction, so it normally requires a furnace to provide heat to a feed stream prior to feeding the feed stream into the reactors. The UOP Oleflex process, disclosed in an article "$C_2/C_5$ Dehydrogenation Updated", Verrow et al, *Hydrocarbon Processing*, April 1982, used stacked catalytic reactors. U.S. Pat. No. 4,191,846 to Farha, Jr. et al teaches the use of group VIII metal containing catalysts to promote catalytic dehydrogenation of paraffins to olefins.

Another key process in the instant invention is the conversion of oxygenates such as methanol and lower olefins to higher hydrocarbons over zeolite type catalyst such as ZSM-5.

These processes are described in detail in the aforenoted and referenced patents and articles.

Referring now to the FIGURE, a schematic diagram of a preferred embodiment of the present invention is presented. Etherification hydrocarbon feedstream 20 preferably comprises a $C_4+$ hydrocarbon stream rich in isoalkenes. The hydrocarbon stream is passed to etherification reactor 21 and mixed with at least 2% excess of methanol based on the isoalkene content of the hydrocarbon stream. A unique advantage of the present invention is the capability to use large stoichiometric excesses of methanol in the etherification reaction, thereby promoting the improved formation of ethers. Excess methanol in the range of 2 to 50% may be conviently used. The etherification reaction is conducted preferably at about 60° C. The etherification effluent is passed 23 to a fractionator 24 wherein a bottom stream 25 is separated comprising ether-rich gasoline. The overhead from the fractionator comprises essentially etherification excess methanol and all or a major portion of unreacted hydrocarbon. The mixture is passed to an olefins to gasoline conversion reactor 27 supplemented, optionally, by a feedstream 28 of $C_3-$ olefinic hydrocarbons. Olefins are converted to gasoline at a pressure between 420 kPa and 2100 kPa (60 and 300 psia) and a temperature between 204° C. and 500° C. Under these conditions methanol in the mixture is also converted to higher hydrocarbons including $C_4-C_5$ olefins. The conversion effluent is passed 29 to a fractionation unit 30 for the separation of $C_3-$ fuel gas 31, $C_4-C_5$ paraffins 32 and a $C_5-C_9$ gasoline product 33. The $C_4-C_5$ paraffins are passed to a dehydrogenation zone 34 where are dehydrogenated to olefins. $C_4-C_5$ olefins are recovered from the dehydrogenation effluent stream 35 and passed to the etherification zone 21. Optionally, a $C_3-$ olefin stream may also be recovered from the dehydrogenation stream and recycled to the olefins to gasoline conversion zone 27. Alternatively, $C_2-C_3$ components leaving the MOG reactor can be sent to the dehydrogenation unit for further conversion to olefins which can be upgraded in the MOG unit. Also, the dehydrogenation reaction reactor effluent can be fed to the etherification unit without separating or efficiently separating $C_3-$ components from $C_4-$ components. This will allow utilizing the MOG separation section as the only gas plant in the process.

One embodiment of the present invention involves an improvement on conventional etherification processes to produce MTBE where the etherification reaction effluent stream is extracted with water to remove excess or unreacted methanol and unreacted methanol recovered by distillation for recycle to the etherification reactor. In the present invention the hydrocarbon portion of the effluent stream after aqueous extraction is separated into $C_4+$ hydrocarbon overhead stream containing unrecovered methanol for further conversion in contact with medium pore shape selective catalyst followed by dehydrogenation of $C_4-C_5$ aliphatic hydrocarbons as described above.

The catalyst useful in the practice of the instant invention in the conversion of methanol to olefins and in the conversion of olefins to gasoline and distillate belongs to a group of related zeolites. Recent developments in zeolite technology have provided a group of medium pore siliceous materials having similar pore geometry. Most prominent among these intermediate pore sized zeolites is ZSM-5, which is usually synthesized with Bronsted active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedrally species having varying degrees of acidity. ZSM-5 crystalline structure is readily recognized by its x-ray defraction pattern, which is described in U.S. Pat. No. 3,702,866, (Argauer, et al), incorporated by reference.

While the invention has been described by reference to particular embodiments, there is no intent to limit the inventive concept except as set forth in the following claims.

What is claimed is:

1. A process for the conversion of $C_2+$ hydrocarbons to ether-rich liquid fuels and olefinic gasoline comprising;
   (a) reacting a fresh hydrocarbon stream containing $C_4+$ iso-alkene with an excess of methanol in an etherification zone in contact with an acidic etherification catalyst under etherification conditions whereby an effluent stream containing methyl tertiary alkyl ether is produced;
   (b) separating said etherification effluent stream to provide a first stream comprising ether-rich gasoline range hydrocarbons and a second stream comprising unreacted methanol and $C_4-$ or $C_5-$ hydrocarbons;
   (c) contacting said second stream with an acidic metallosilicate catalyst in oxygenates and olefins conversion zone under olefins oligomerization conditions at elevated temperature;
   (d) separating said conversion zone olefins oligomerization effluent stream in a first stream comprising $C_4-C_5$ paraffinic hydrocarbon, $C_3-$ hydrocarbons and light gases, and a liquid product stream comprising $C_6+$ olefinic gasoline;
   (e) contacting said $C_4-C_5$ hydrocarbon stream with a dehydrogenation catalyst under dehydrogenation conditions whereby $C_4-C_5$ paraffins are converted to $C_4-C_5$ olefins;
   (f) separating effluent from step (e) and passing a portion thereof comprising $C_4+$ olefins to said etherification zone in conjunction with said fresh hydrocarbon stream and methanol for conversion to methyl tertiary alkyl ethers.

2. The process of claim 1 wherein $C_3-$ olefins from step (f) are recovered and recycled to step (c) oxygenates and olefins conversion zone.

3. The process of claim 1 wherein said step (b) second stream comprises an azeotropic mixture of methanol and olefinic hydrocarbons and said first stream comprises C$_5$+ ether-rich gasoline.

4. The process of claim 1 wherein the etherification conditions comprise a high stoichiometric excess of said methanol over C$_4$+ iso-alkenes whereby the etherification reaction equilibrium is shifted substantially toward the formation of C$_5$+ ethers.

5. The process of claim 4 wherein said stoichiometric excess of methanol is between about 3 and 33 percent.

6. The process of claim 5 wherein said stoichiometric excess of methanol is between about 3 and 10 percent.

7. The process of claim 1 wherein said metallosilicate catalyst comprises a shape-selective, medium pore, acid aluminosilicate zeolite-type catalyst.

8. The process of claim 1 wherein step (b) first stream comprises C$_5$+ ether-rich gasoline having high motor octane and research octane values.

9. An integrated continuous process for producing lower alkyl ethers and gasoline range hydrocarbons comprising the steps of:
(a) contacting a first liquid reaction mixture with an acid etherification catalyst in an etherification zone under etherification conditions, said first reaction mixture comprising C$_4$–C$_9$ hydrocarbons containing C$_4$–C$_7$ isoalkene components and C$_5$+ gasoline range non-etherifiable aliphatic components, and a lower aliphatic alcohol reactant, said alcohol being present in stoichiometric excess of the iso-alkene component;
(b) recovering etherification reaction effluent from step (a) containing C$_5$+ tertiary alkyl ether, gasoline range hydrocarbons, unreacted alcohol and light olefinic hydrocarbons;
(c) distilling the etherification reaction effluent to provide a first product stream comprising a liquid mixture of C$_5$+ ether and gasoline range hydrocarbons, and a second volatile low molecular weight reaction mixture comprising unreacted alcohol and light aliphatic hydrocarbons; and
(d) contacting the second reaction mixture with acid medium pore metallosilicate zeolite catalyst at elevated temperature to convert the unreacted alcohol and light olefinic hydrocarbons to a second reaction effluent stream having average molecular weight greater than the second reaction mixture and containing C$_4$–C$_5$ branched aliphatic hydrocarbon and C$_6$+ hydrocarbon;
(e) separating the second reaction effluent stream to obtain a second C$_6$+ hydrocarbon liquid product and a C$_4$–C$_5$ aliphatic hydrocarbon stream;
(f) passing a C$_4$–C$_5$ aliphatic hydrocarbon portion thereof to a dehydrogenation reaction zone under dehydrogenation reaction conditions; and
(g) passing at least at portion of step (f) dehydrogenation product stream comprising C$_4$–C$_5$ olefins to step (a) etherification zone for etherification and conversion to high octane gasoline.

10. The process of claim 9 wherein the first reaction mixture consists essentially of a mixture of butylene isomers, light olefinic naphtha and methanol, said methanol being present in at least 2% excess of the isoalkene component; wherein the second reaction mixture comprises unreacted methanol, paraffins and butylenes; and wherein the zeolite catalyst comprises aluminosilicate having the structure of ZSM-5.

11. The process of claim 10 wherein the second reaction mixture is supplemented with an added light olefin stream.

12. The process of claim 9 wherein the first product stream comprises MTBE, TAME and unreacted naphtha.

13. In the process for the production of methyl tertiary alkyl ethers comprising reacting a mixture comprising methanol and C$_4$+ iso-butylene-rich hydrocarbons in contact with acid etherification catalyst under etherification conditions in an etherification zone to produce a product stream comprising C$_5$+ methyl tertiary alkyl ethers, unreacted methanol and hydrocarbons, separating said product stream by aqueous extraction and distillation of unreacted methanol, recycling unreacted methanol and recovering a hydrocarbon stream rich in C$_5$+ methyl tertiary alkyl ether, the improvement comprising;
separating said product stream by distillation to produce an overhead vapor stream comprising unrecovered methanol and C$_4$+ hydrocarbons and a bottom liquid stream comprising hydrocarbons rich in C$_5$+ ether;
passing said overhead stream to an oxygenates and olefins conversion zone in contact with medium pore shape selective metallosilicate catalyst particles under conversion condition whereby oxygenates and/or olefins are converted to conversion products having higher average molecular weight;
recovering said conversion products and passing a portion thereof comprising C$_4$ aliphatic hydrocarbons to a dehydrogenation zone under dehydrogenation conditions whereby C$_4$ olefins are produced;
recovering said C$_4$ olefin; and passing said olefins to said etherification zone in conjunction with fresh methanol and C$_4$+ iso-olefins-rich hydrocarbons.

14. The process of claim 13 wherein etherification reaction mixture comprise a large stoichiometric excess of methanol whereby the yield of methyl tertiary alkyl ethers is increased;
wherein the etherification product stream is separated by aqueous extraction and distillation of unreacted methanol to recover an aqueous stream containing a major portion of unreacted methanol for recycling the unreacted methanol for further etherification and recovering a hydrocarbon stream rich in C$_5$+ methyl tertiary-alkyl ether.

15. The process of claim 14 wherein the methyl tertiary alkyl ethers comprise methyl tertiary butyl ether and methyl tertiaryamyl ether.

16. The process of claim 1 wherein C$_2$–C$_3$ portion of step (d) C$_3$– hydrocarbon is passed to step (e) for conversion to olefins for recycle to step (c) conversion zone.

17. In the process of manufacturing high octane gasoline from mixed hydrocarbon feedstock containing lower isoalkene, wherein the isoalkene is reacted in a first etherification reaction zone with excess methanol by acid catalysis to provide a first reaction effluent stream containing C$_5$+ t-alkyl methyl ether, unreacted methanol, light hydrocarbon and C$_6$+ gasoline range hydrocarbons, and wherein the first reaction effluent is fractionated to provide a first liquid product stream containing a high octane mixture of t-alkyl methyl ether and C$_6$+ hydrocarbons and an overhead vapor stream comprising methanol and light hydrocarbon; the improvement which comprises:

contacting the overhead vapor stream in a second reaction zone with an acid medium pore shape selective catalyst under methanol and hydrocarbon conversion conditions to upgrade the vapor to produce a second effluent stream comprising $C_4$-$C_5$ aliphatic hydrocarbons and $C_6$+ hydrocarbons;

separating the second effluent stream to provide a second liquid product stream rich in $C_6$+ gasoline range hydrocarbons and a $C_4$-$C_5$ aliphatics-rich stream;

converting at least a portion of the $C_4$-$C_5$ aliphatic stream in a third reaction zone under dehydrogenation conditions to provide a stream rich in $C_4$-$C_5$ isoalkene; and recycling the $C_4$-$C_5$ isoalkene-rich steam to the etherification zone for further converstion to ether rich gasoline.

18. The process of claim 16 wherein fresh feedstock includes a mixture of butanes, n-butenes and isobutylene; wherein the medium pore catalyst comprises at least one acid metallosilicate having the structure of ZSM-5 zeolite; and wherein conversion conditions in the second reaction zone provide $C_4$-$C_5$ branched paraffin hydrocarbons for dehydrogenation to $C_4$-$C_5$ isoalkenes.

19. A reactor system for the conversion of $C_2$+ hydrocarbons to a high quality gasoline, comprising in combination:

first reactor means for containing catalyst for etherification of $C_4$+ iso-alkenes with methanol;

distillation means operatively connected to said first reactor for separating etherification effluent therefrom;

second reactor means receivable connected to said distillation means for converting distillation overhead stream;

separator means for separating said second reactor effluent operatively connected to thereto;

third reactor means operatively connected to said separator and in communication with said first reactor for containing dehydrogenation catalyst for dehydrogenation of a portion of said separator effluent;

conduit means connected to said first and third reactors for passing a portion of effluent from said third to said first reactor.

20. The reactor system according to claim 19 further comprising:

second separator means receivably connected to said third reactor and in communication with said first and second reactor for separating effluent therefrom and passing $C_4$-$C_5$ olefins to said first reactor and $C_2$-$C_3$ olefins to said second reactor.

* * * * *